United States Patent [19]
Thompson et al.

[11] Patent Number: 5,921,978
[45] Date of Patent: Jul. 13, 1999

[54] CATHETER TIP STEERING PLANE MARKER

[75] Inventors: Russell B. Thompson, Los Altos; Sidney D. Fleischman, Menlo Park; Bruce H. Wand, San Jose, all of Calif.

[73] Assignee: EP Technologies, Inc., San Jose, Calif.

[21] Appl. No.: 08/879,738

[22] Filed: Jun. 20, 1997

[51] Int. Cl.⁶ .................................................. A61M 25/00
[52] U.S. Cl. .......................... 604/529; 604/523; 604/49; 604/95
[58] Field of Search ....................... 604/280, 264, 604/95, 49, 523, 529, 528; 128/656–658

[56] References Cited

U.S. PATENT DOCUMENTS 5,045,071  9/1991  McCormick et al. ................... 604/280
5,045,072  9/1991  Castillo et al. ......................... 604/280
5,203,777  4/1993  Lee .......................................... 604/280

*Primary Examiner*—John D. Yasko
*Attorney, Agent, or Firm*—Lyon & Lyon LLP

[57] ABSTRACT

A catheter including fluoroscopic marker components disposed in the catheter distal end portion to provide enhanced fluoroscopic visibility of the catheter end portion. Various embodiments of the marker include a cylindrical plug disposed within the catheter tip, a half section catheter tip, a longitudinal stripe along a sidewall of the catheter end portion, and multiple combinations of marker plugs and marker stripes to provide enhanced in vivo fluoroscopically visible catheter disposition information to the physician. An enhanced embodiment of the present invention includes an orientation marker that is disposed on the steering handle, particularly on the control knob, to provide visual and tactile information to the catheter user regarding the direction to manipulate the control knob in order to maneuver the catheter distal end portion.

17 Claims, 11 Drawing Sheets

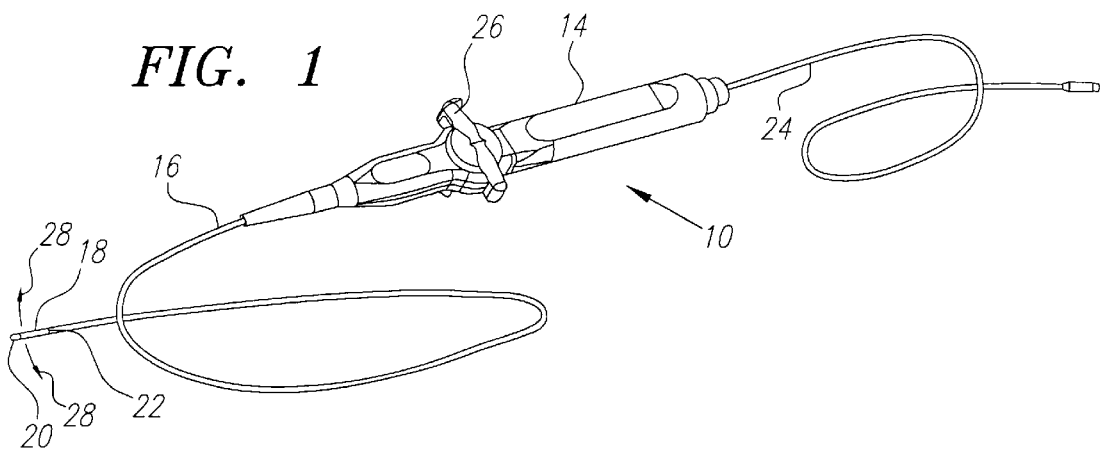
FIG. 1
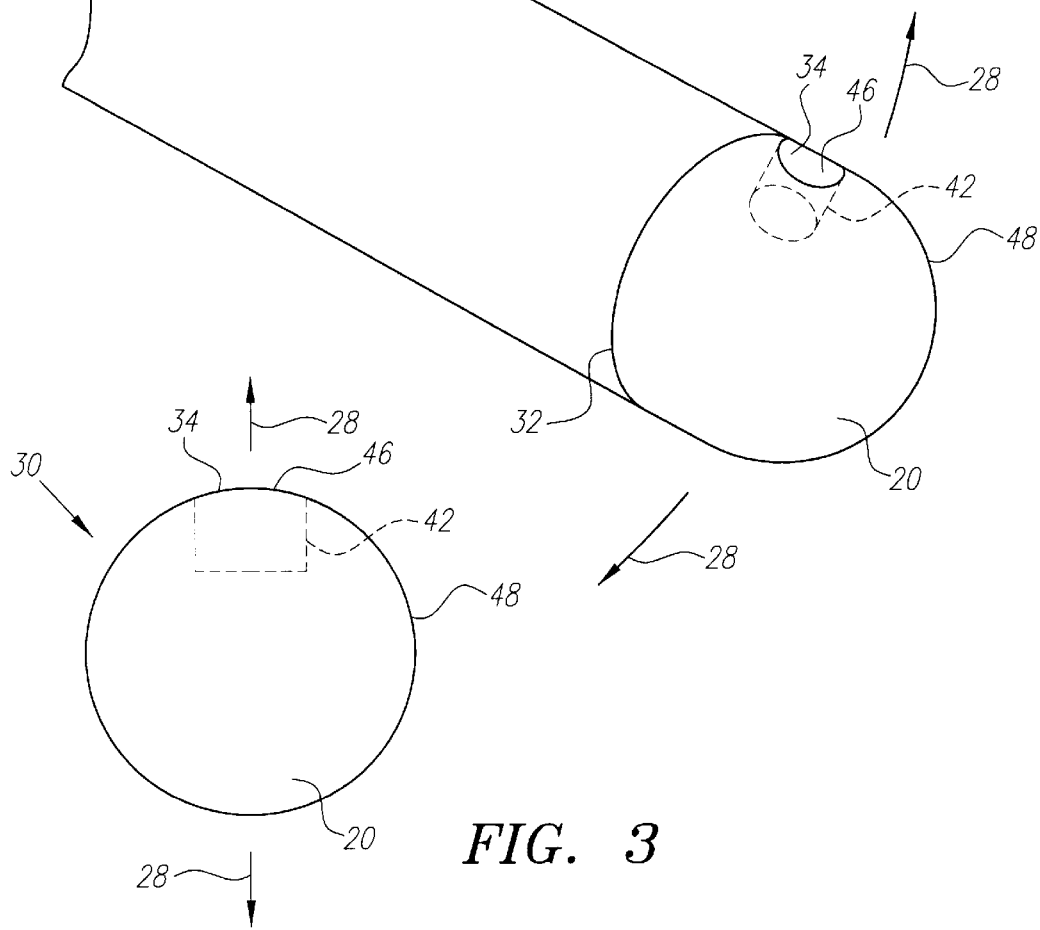
FIG. 2
FIG. 3

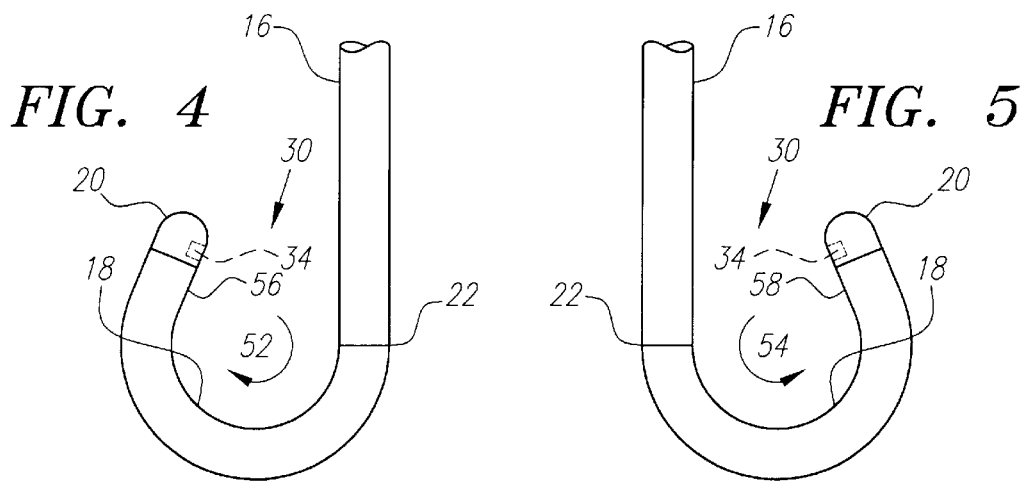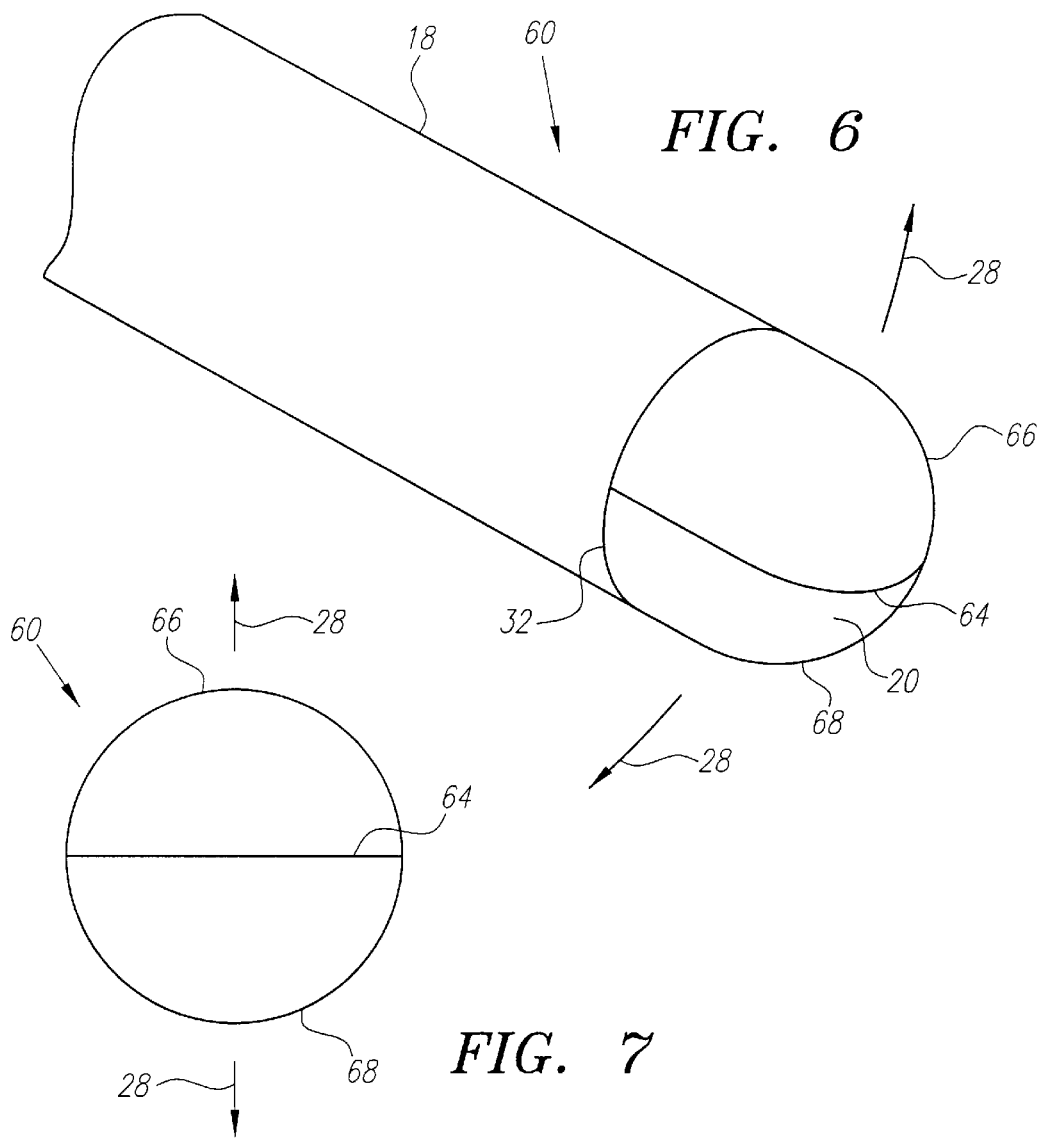

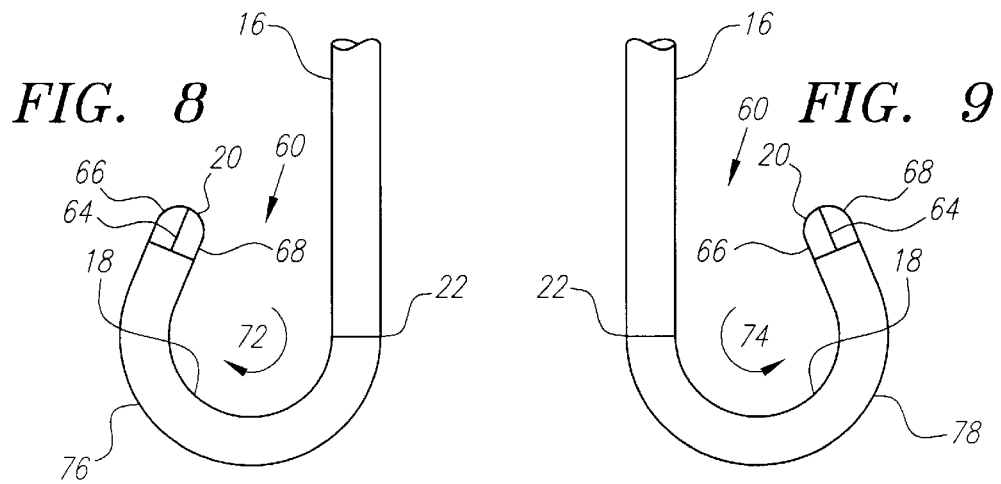
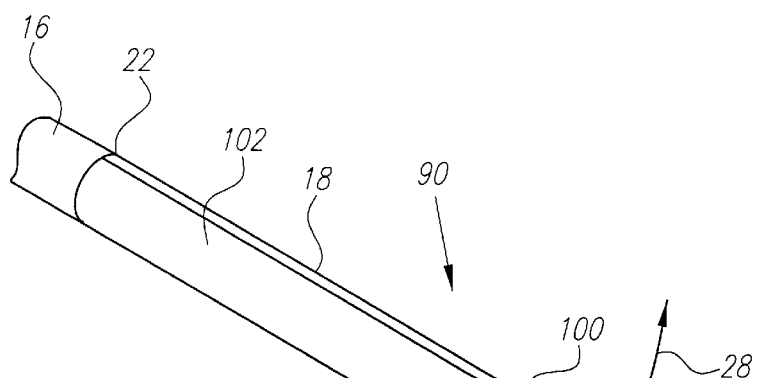
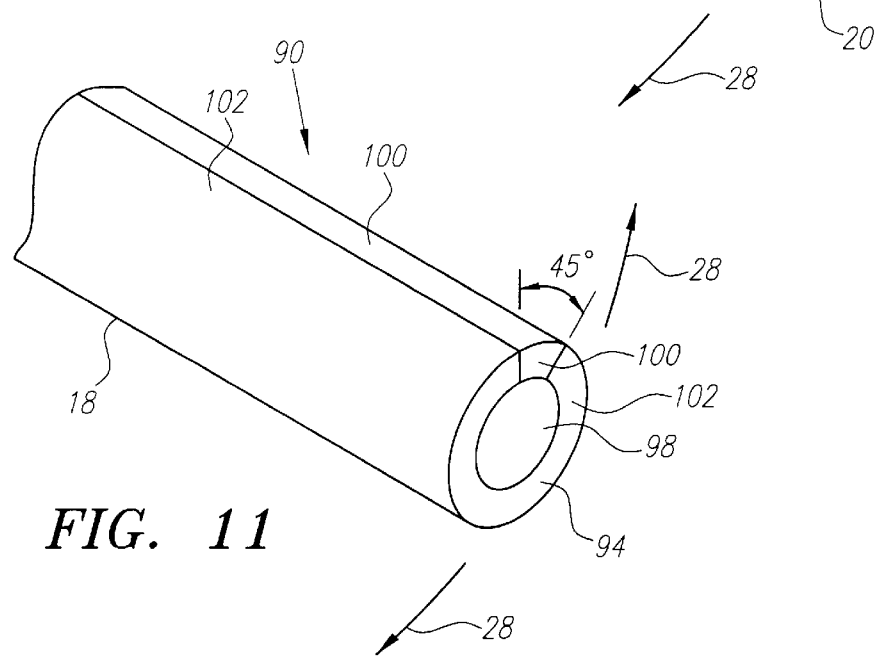

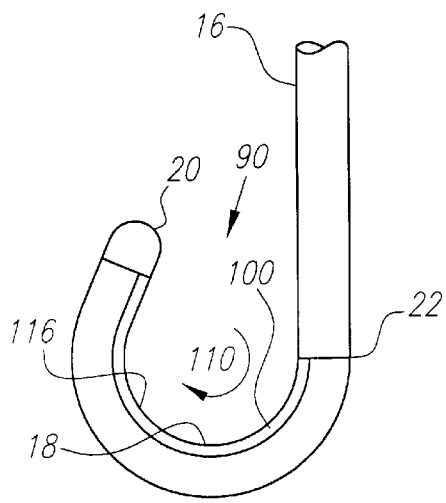
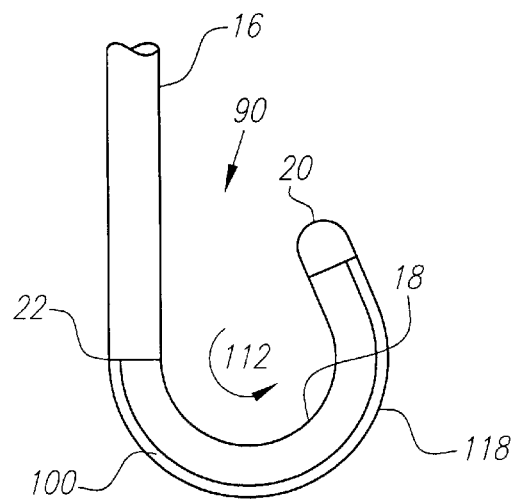
FIG. 12  FIG. 13
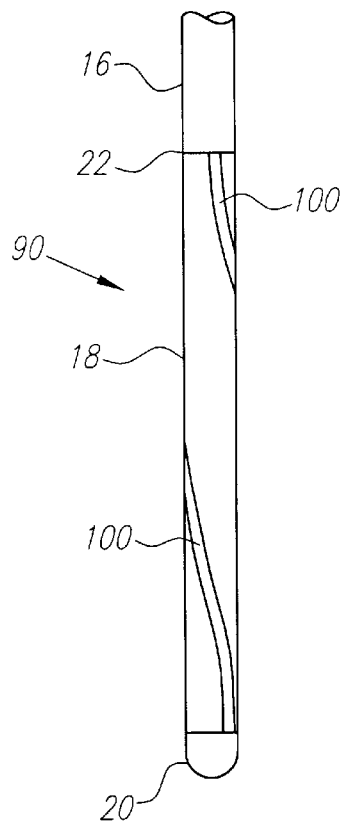
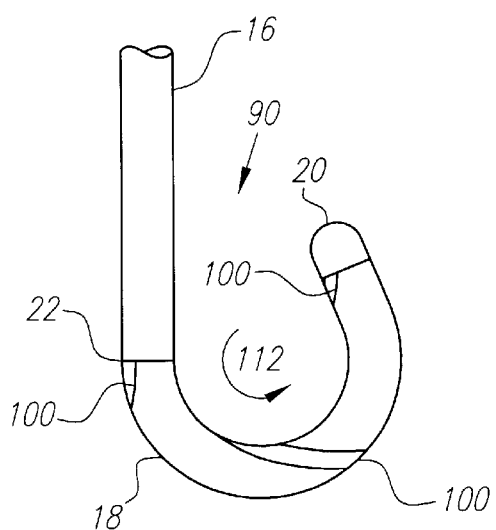
FIG. 14  FIG. 15

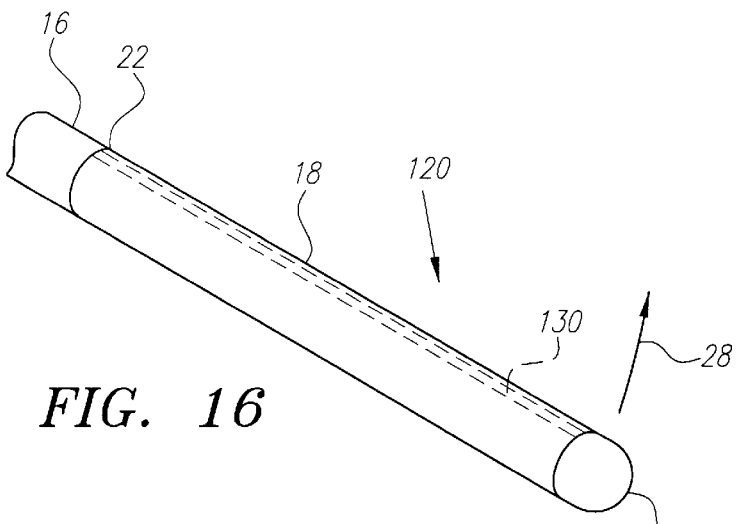
FIG. 16
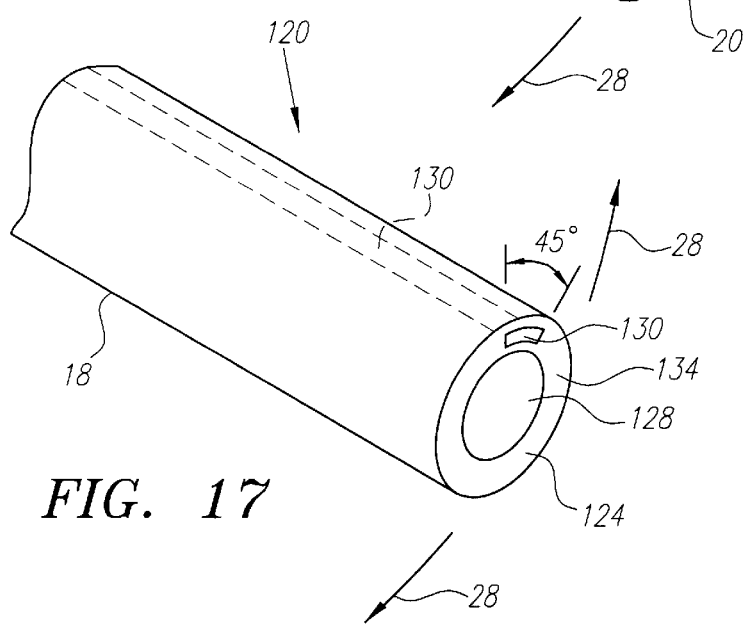
FIG. 17
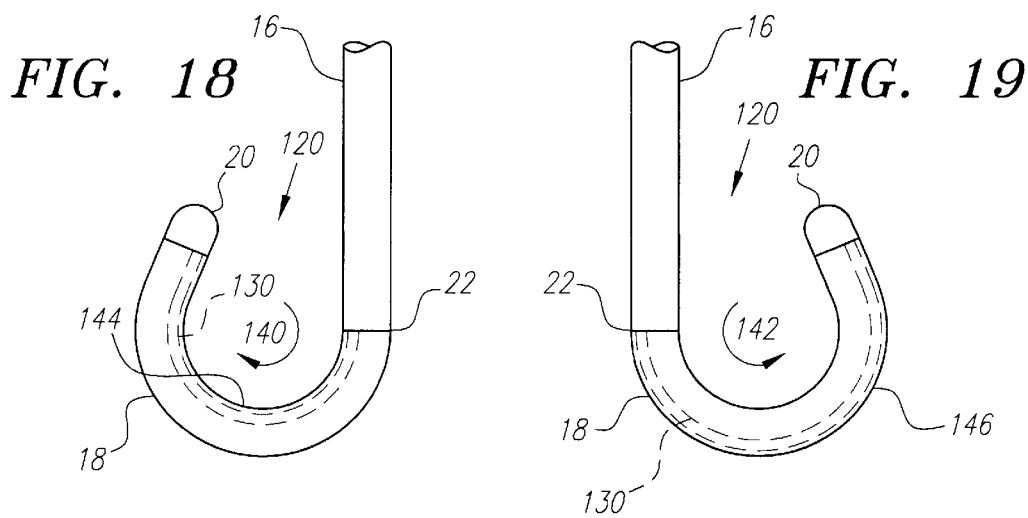
FIG. 18
FIG. 19

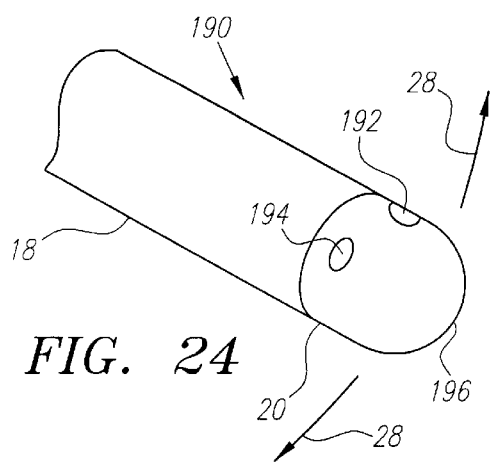
FIG. 24
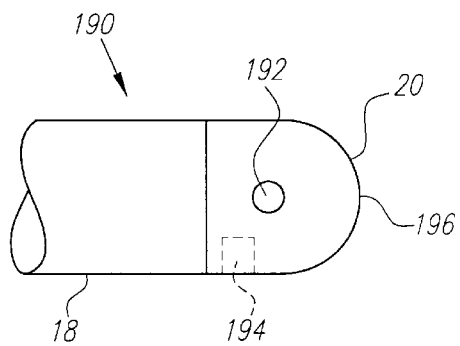
FIG. 25
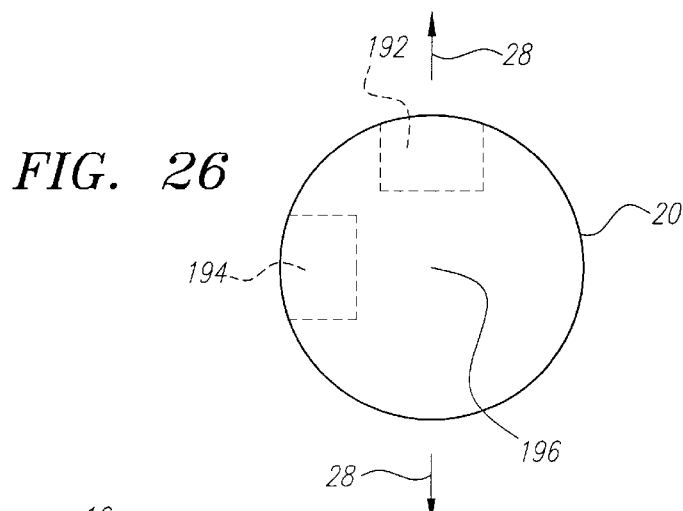
FIG. 26
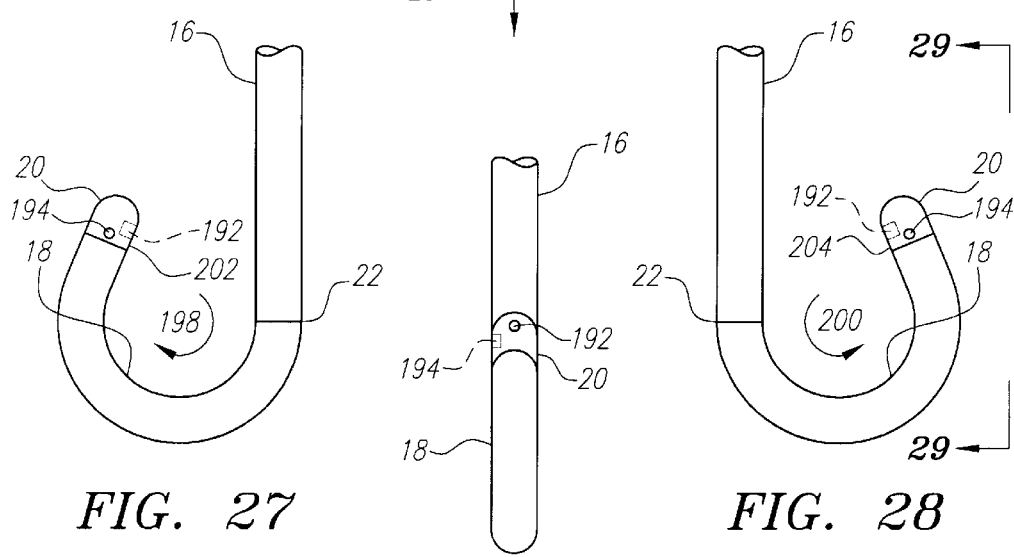
FIG. 27
FIG. 28
FIG. 29

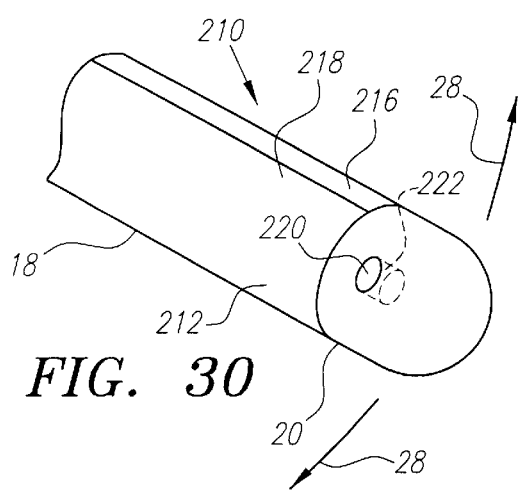
*FIG. 30*
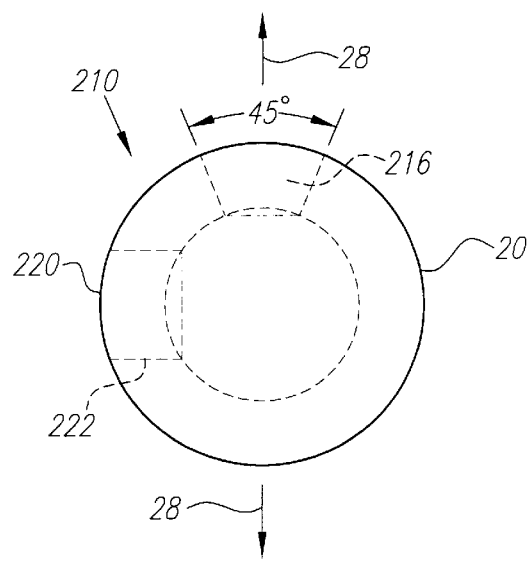
*FIG. 31*
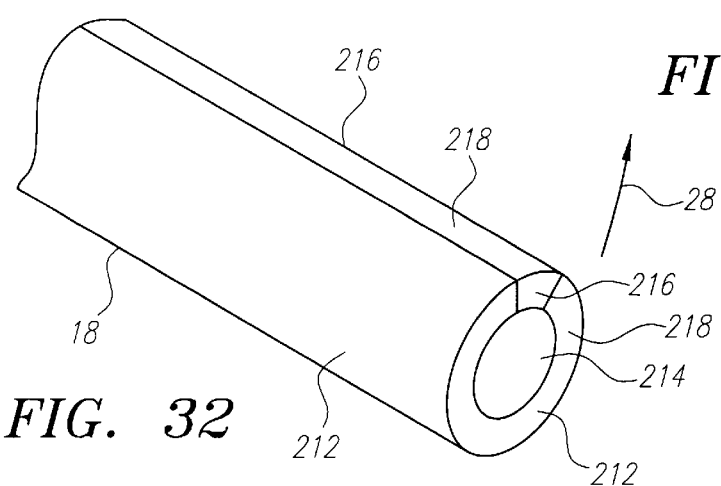
*FIG. 32*
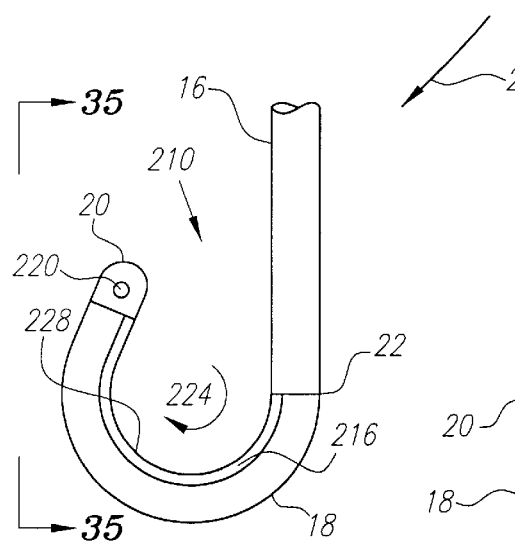
*FIG. 33*
*FIG. 35*
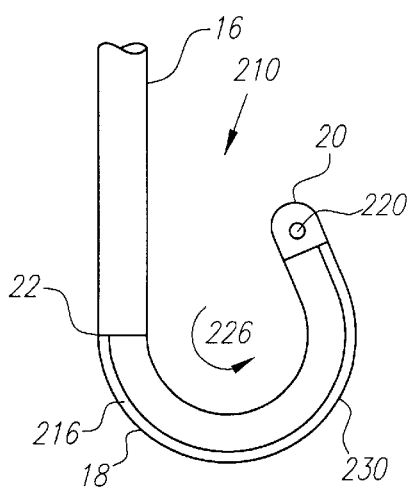
*FIG. 34*

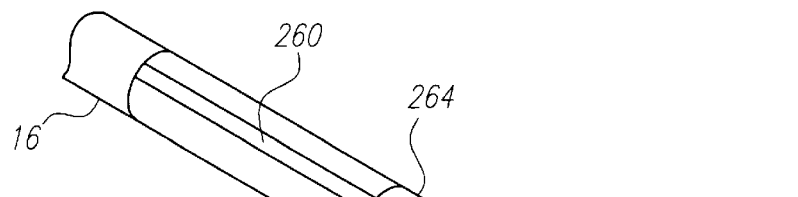
FIG. 40
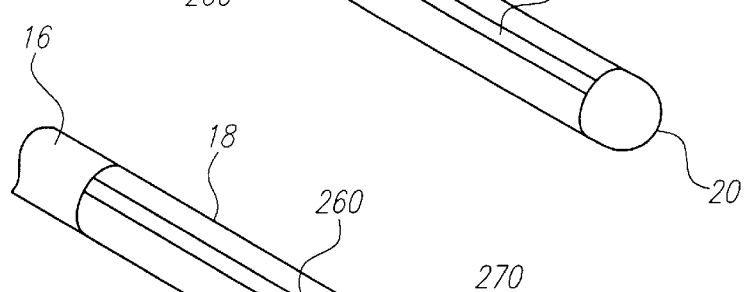
FIG. 41
FIG. 42
FIG. 43
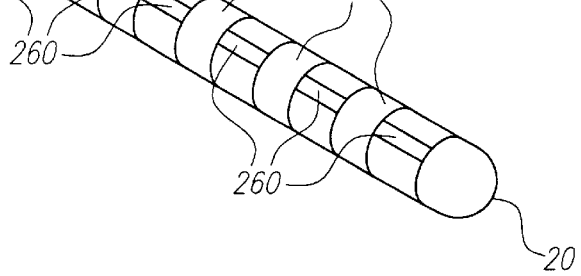

CATHETER TIP STEERING PLANE MARKER

BACKGROUND OF THE INVENTION

1. Field of the Invention

The present invention relates generally to devices and methods for locating catheters in vivo, and more particularly to devices and methods that provide a visible indication of the in vivo location and orientation of a catheter distal end section.

2. Description of the Prior Art

It is often difficult to determine the location and orientation of a catheter distal end portion and to determine the direction to steer it to get to a desired location. This can be particularly problematic when steering a bi-directional catheter which has become twisted and convoluted within the patient's anatomy, whereupon it is difficult to tell which direction to manipulate the catheter handle relative to the steerable distal end portion of the catheter. At times, the catheter movement can be critical, especially if catheter placement has been difficult and the physician needs to adjust the placement a minor amount. In this situation, he needs to know which direction to properly steer the catheter end portion.

To accomplish catheter steering, a fluoroscope is typically utilized to provide real time in vivo viewing of the catheter end portion location and orientation. However, the fluoroscopic view is generally two dimensional, and owing to various twists that a guide tube and end portion may have, the in vivo fluoroscopic viewing of the catheter end portion leaves much to be desired.

The present invention includes marker elements within the catheter end portion that are more fluoroscopically visible than the currently utilized end portion materials. The efficacious positioning of such markers, as disclosed herebelow, provides enhanced fluoroscopically visible information to the physician regarding the location and orientation of the catheter end portion, thus enabling the physician to determine which direction to manipulate a steering mechanism to adjust the catheter end portion location and orientation.

SUMMARY OF THE INVENTION

The catheter of the present invention includes marker components disposed in the catheter distal end portion to provide enhanced fluoroscopic visibility to the catheter end portion. The invention is advantageously used with single direction steering catheters and has particular advantages when utilized with bi-directional steering catheters to provide the physician with enhanced visual information in order to determine which direction to adjust a steering control knob to properly steer the end portion of the catheter. Various embodiments of the marker include a cylindrical plug disposed within the catheter tip, a half section catheter tip, a longitudinal stripe along a sidewall of the catheter end portion, and multiple combinations of marker plugs and marker stripes to provide enhanced in vivo fluoroscopically visible catheter disposition information to the physician. An enhanced embodiment of the present invention includes an orientation marker that is disposed on the steering handle, particularly on the control knob, to provide visual and tactile information to the catheter user regarding the direction to manipulate the control knob in order to maneuver the catheter distal end portion.

It is an advantage of the present invention that enhanced in vivo fluoroscopically visible information regarding the disposition of a catheter end portion is provided.

It is another advantage of the present invention that the steering plane of a steerable catheter end portion is visually identifiable in an in vivo catheter placement.

It is a further advantage of the present invention that enhanced fluoroscopically visible information regarding the steering plane location and orientation of a bi-directional catheter is provided.

It is yet another advantage of the present invention that both the in-plane steering and out-of-plane steering orientations of an in vivo catheter are visually identifiable, such that the steering of the catheter end portion is more precisely accomplished.

It is yet a further advantage of the present invention that the catheter handle is provided with a visual and/or tactile indicator that provides information to the user regarding the direction to manipulate the catheter control knob in order to change the orientation of the catheter end portion.

These and other features and advantages of the present invention will become apparent from the following detailed description of the preferred embodiments taken in conjunction with the accompanying drawings.

IN THE DRAWINGS

FIG. 1 is a perspective view of a catheter of the present invention;

FIG. 2 is an enlarged perspective view of a catheter distal end, depicting a first embodiment of the present invention;

FIG. 3 is an end elevational view of the embodiment depicted in FIG. 2;

FIG. 4 is a side elevational view depicting a catheter end portion including the embodiment depicted in FIGS. 2 and 3 in a left hand curve;

FIG. 5 is a side elevational view depicting a catheter end portion including the embodiment depicted in FIGS. 2 and 3 in a right hand curve;

FIG. 6 is an enlarged perspective view of a first alternative embodiment of the present invention;

FIG. 7 is an end elevational view of the embodiment depicted in FIG. 6;

FIG. 8 is a side elevational view depicting a catheter end portion including the embodiment depicted in FIGS. 6 and 7 in a left hand curve;

FIG. 9 is a side elevational view depicting a catheter end portion including the embodiment depicted in FIGS. 6 and 7 in a right hand curve;

FIG. 10 is a perspective view of a catheter end portion depicting another embodiment of the present invention;

FIG. 11 is a perspective view of the catheter end portion depicted in FIG. 10 and having the tip portion removed therefrom;

FIG. 12 is a side elevational view of a catheter end portion including the embodiment depicted in FIGS. 10 and 11 in a left hand curve;

FIG. 13 is a side elevational view of a catheter end portion including the embodiment depicted in FIGS. 10 and 11 in a right hand curve;

FIG. 14 is a top plan view of the catheter end portion depicted in FIG. 10 having a clockwise twist;

FIG. 15 is a side elevational view of the catheter end portion depicted in FIG. 13, having a left hand curve and being twisted in a clockwise direction;

FIG. 16 is a perspective view of a catheter end portion depicting a further embodiment of the present invention;

FIG. 17 is a perspective view of the embodiment depicted in FIG. 16 having the tip portion removed;

FIG. 18 is a side elevational view of a catheter end portion including the embodiment depicted in FIGS. 16 and 17 in a left hand curve;

FIG. 19 is a side elevational view of a catheter end portion including the embodiment depicted in FIGS. 16 and 17 in a right hand curve;

FIG. 24 is a perspective view of a catheter end portion depicting yet a further preferred embodiment of the present invention;

FIG. 25 is a top plan view of the embodiment depicted in FIG. 24;

FIG. 26 is an end elevational view of the embodiment depicted in FIGS. 24 and 25;

FIG. 27 is a side elevational view of a catheter end portion including the embodiment depicted in FIGS. 24–26 in a left hand curve;

FIG. 28 is a side elevational view of a catheter end portion including the embodiment depicted in FIGS. 24–26 in a right hand curve;

FIG. 29 is a side elevational view of the catheter end portion depicted in FIG. 28, taken along lines 29—29 thereof;

FIG. 30 is a perspective view of a catheter end portion depicting yet another preferred embodiment of the present invention;

FIG. 31 is an end elevational view of the embodiment depicted in FIG. 30;

FIG. 32 is a perspective view of the embodiment depicted in FIG. 30 having the tip portion removed;

FIG. 33 is a side elevational view of a catheter end portion including the embodiment depicted in FIGS. 30–32 in a left hand curve;

FIG. 34 is a side elevational view of a catheter end portion including the embodiment depicted in FIGS. 30–32 in a right hand curve;

FIG. 35 is a side elevational view of the catheter end portion depicted in FIG. 33 taken, along lines 35—35 thereof;

FIG. 40 is a perspective view of a catheter distal end portion having a marker stripe which indicates the location of a sensor component;

FIG. 41 is a perspective view of a catheter distal end portion depicting another embodiment in which a longitudinal marker stripe is utilized to indicate the location of a sensor component;

FIG. 42 is a perspective view of a catheter distal end portion, depicting a further embodiment which utilizes a marker stripe to indicate the location of a sensor component;

FIG. 43 is a perspective view of a catheter distal end portion depicting yet another embodiment that utilizes a marker to identify the location of components;

DETAILED DESCRIPTION OF THE PREFERRED EMBODIMENTS

Figure 20:
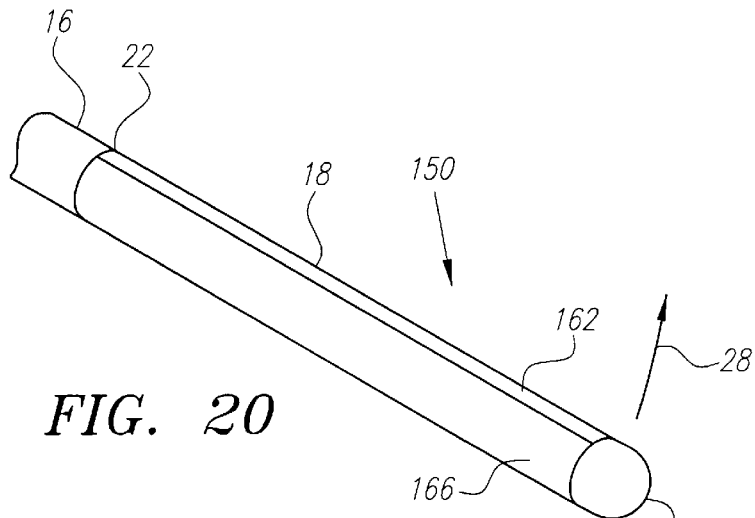
FIG. 20 is a perspective view of a catheter end portion depicting yet another preferred embodiment of the present invention.

FIG. 1 depicts a catheter device 10 of the present invention that includes a steering plane marker means therewithin. The catheter 10 generally includes a handle assembly 14, a guide tube 16 and a catheter distal end portion 18 having a tip 20 engaged thereto. The end portion 18 is fixedly engaged to the guide tube 16 at a bonded joint 22. A standard catheter steering mechanism is disposed throughout the handle assembly 14, guide tube 16 and end portion 18, which steering assembly is operated by a control knob 26 included within the handle assembly 14. An electrical interconnection cable 24 may be engaged with a pin connector (not shown) that is disposed in the proximal end of the handle assembly 14. As will be understood from the following description, the steering plane marker embodiments are particularly useful when employed with a bi-directional catheter which may be steered in two opposite directions 28 within a steering plane by the manipulation of the control knob 26.

When the catheter 10 is used, a physician grips the handle assembly 14 and operates the control knob 26 to steer the guide tube assembly 16 and end portion 18 through a patient's vein or artery, such as the femoral artery. The physician further manipulates the control knob 26 and handle assembly 14 to steer the catheter end portion 18 into a desired position, such as within the patient's heart. In doing so, the physician utilizes a fluoroscope to view the location and orientation of the catheter end portion 18 while steering it to the desired location. The steering plane marker embodiments described herebelow provide greater visualization of the orientation of the catheter end portion 18, and thereby allow the physician to steer the device more efficiently. In addition to providing improved fluoroscopic visibility of the catheter end portion 18, an enhanced embodiment of the present invention also includes indicia disposed on the handle assembly 14 which provides further information to the physician.

A first catheter steering plane marker embodiment 30 is depicted in FIGS. 2 and 3, wherein FIG. 2 is a perspective view of a catheter end portion 18 and FIG. 3 is an end elevational view of the embodiment 30 depicted in FIG. 2. The generally cylindrical catheter end portion 18 includes a distal end 32 having a rounded catheter tip 20 engaged thereto. Such catheter tips 20 are generally composed of stainless steel. A steering plane marker means 34 is disposed within the tip 20, and the catheter tip 20 is engaged to the catheter end portion 18, such that the marker means 34 resides in the steering plane 28 of the catheter end portion 18. In this preferred embodiment, the marker means 34 is shaped as a cylindrical plug member that is disposed within a cylindrical cavity 42 formed within the tip 20. The outer surface 46 of the marker plug 34 is shaped to smoothly conform with the outer surface 48 of the tip 20. The marker plug 34 is composed of a material which provides a darker fluoroscopic image than the tip 20, such that the marker plug 34 is more visible to the physician than the surrounding tip. Preferred marker plug materials include platinum, barium, bismuth, gold, and other materials that provide a contrasting fluoroscopic image.

FIGS. 4 and 5 depict the catheter end portion 18 of the present embodiment 30 having the steering marker plug 34 disposed in the tip 20 thereof. It is to be understood that FIGS. 4 and 5 depict the operational orientations of a bi-directional steering catheter 10, wherein FIG. 4 depicts a left hand curve 52 and FIG. 5 depicts a right hand curve 54. A comparison of FIGS. 4 and 5 shows that the steering plane marker 34 of FIG. 4 is disposed on the interior portion 56 of the curve 52, whereas in FIG. 5, the steering plane marker 34 is disposed on the outer portion 58 of the curve 54. Because the catheter guide tube 16 may become convoluted during utilization particularly from the arterial passage, it is to be understood that the steering plane marker 34 provides information to the physician regarding which direction to turn the steering handle control knob 26 to tighten or loosen the curve 52 or 54, depending upon the orientation of the fluoroscopically visible steering plane marker 34.

FIGS. 6 and 7 depict a first alternative steering plane marker embodiment 60, in which FIG. 6 is a perspective view of the catheter end portion 18, and FIG. 7 is an end view thereof. As depicted in FIG. 6, a catheter tip 20 is engaged to the distal end 32 of the catheter end portion 18. The catheter tip 20 has a bisecting mid-plane 64 which is perpendicular to the catheter's bi-directional steering plane 28, such that a top half 66 of the tip 20 is distinct from the bottom half 68 of the tip 20. In the preferred embodiment, one of the two halves, such as 68, is composed of a standard material such as stainless steel, whereas the other half 66 forms a marker means that is composed of a more fluoroscopically visible material, such as platinum or the other materials identified hereabove regarding marker plug 34. As with marker embodiment 30 described above, the tip 20 with marker 66 is engaged to the distal end 32 of the catheter end portion 18, such that the marker 66 resides in the steering plane 28 of the catheter end portion 18. A comparison of FIGS. 3 and 7 reveals the similarity of embodiments 30 and 60, wherein it is seen that the marker plug 34 in FIG. 3 may be thought of as being replaced by a marker half-tip 66 of FIG. 7. The advantage of the marker embodiment 60 of FIG. 7 is that the marker 66 is physically larger, and therefore more fluoroscopically visible to the user.

FIGS. 8 and 9 depict the marker embodiment 60 of FIGS. 6 and 7 when disposed in a left hand curve 72 (FIG. 8) and a right hand curve 74 (FIG. 9) of a bi-directional catheter 10. FIGS. 8 and 9 are comparable to FIGS. 4 and 5 in that they depict how the orientation of the fluoroscopically visible marker 66 provides information to the user regarding the location and orientation of the end portion 18 of the catheter. For further comprehension of the invention, the marker 66 is shown disposed on the outside surface 76 of the left hand curve 72 of FIG. 8, whereas the marker 66 is shown on the inside surface 78 of the right hand curve 74 of FIG. 9.

FIGS. 10 and 11 depict another steering plane marker embodiment 90 of the present invention, wherein FIG. 10 is a perspective view of a catheter end portion 18 having a tip 20 engaged thereto, and FIG. 11 is a perspective view showing the catheter end portion 18 with the tip 20 removed.

As depicted in FIGS. 10 and 11, the steering marker embodiment 90 includes a tubular catheter end portion 18 including a cylindrical sidewall 94 and a centrally disposed steering mechanism bore 98 in which the end of a catheter steering mechanism (not shown) would reside. The marker means includes an arcuate portion 100 of the sidewall 94, and it is formulated to include a material having enhanced fluoroscopic visibility over the material which comprises the remaining portion 102 of the sidewall 94. The catheter 10, and particularly the catheter end portion 18 is manufactured such that the longitudinal tube marker portion 100 will reside in the steering plane 28 of the catheter end portion 18. In the preferred embodiment, the tubular end portion 18 is manufactured by an extrusion process, wherein the marker portion 100 includes a fluoroscopically opaque material. The arc subtended by the marker portion 100 is preferably approximately 35° to 90°, in order to provide a suitable fluoroscopically visible image, which will appear as a dark stripe generally within the steering plane 28 of the catheter 10.

The composition and concentration of the fluoroscopically opaque material included in the composition of the marker portion 100 have the constraints that the material have acceptable bio-compatability with the patient because blood contact with the material will occur, and that the marker portion 100 have approximately the same durometer as the tubing sidewall portions 94. In the preferred embodiment, the catheter end portion tubing material is preferably Pellethane® (a polyurethane) and the marker portion 100 includes Pellethane with approximately 30%+/−2% of barium sulfate, tantalum oxide or other suitable material. Pellethane is a registered trademark of Dow Chemical Corporation.

FIGS. 12 and 13 depict the marker embodiment 90 of FIGS. 10 and 11 when disposed in a left hand curve 110 (FIG. 12) and a right hand curve 112 (FIG. 13) of a bi-directional catheter. FIGS. 12 and 13 are comparable to FIGS. 4, 5 and 8, 9 in that they depict how the orientation of the fluoroscopically visible marker 100 provides information to the user regarding the location and orientation of the end portion 18 of the catheter. For further comprehension of the invention, the marker 100 appears as a stripe on the inside surface 116 of the left hand curve 110 of FIG. 12, whereas the marker 100 appears as a stripe on the outside surface 118 of the right hand curve 112 of FIG. 13.

A catheter tip portion 18 will often become twisted during use, and the marker embodiment 90 (and further marker embodiments disclosed herebelow) are particularly useful in providing visual information to the physician regarding the direction and degree of twist. FIG. 14 depicts a straight catheter end portion 18 having a clockwise twist, wherein the marker stripe 100 provides visual information regarding the direction and degree of twisting. It is also possible for a twisted catheter end portion 18 to be formed into a curve or spiral configuration, and FIG. 15 depicts a twisted end portion 18 formed into a right hand curve 112. As depicted therein, the stripe 100 provides visual information regarding the end portion configuration, including both the twist and the right hand curve 112. It is therefore to be understood that the marker stripe embodiment 90 provides significant fluoroscopically visual information to the physician regarding the orientation of the catheter tip portion 18.

FIGS. 16 and 17 depict a further steering plane marker embodiment 120 of the present invention, wherein FIG. 16 is a perspective view of a catheter end portion 18 having a tip 20 engaged thereto, and FIG. 17 is a perspective view showing the catheter end portion 18 with the tip 20 removed. The steering marker embodiment 120 includes a tubular catheter end portion 18 including a cylindrical sidewall 124 and a centrally disposed steering mechanism bore 128. An arcuate shaped marker means 130 is enclosed within the sidewall 124 and includes a material having enhanced fluoroscopic visibility over the material which comprises the remaining portion 134 of the sidewall 124. The catheter 10, and particularly the catheter end portion 18 is manufactured such that the arcuate, longitudinal tube marker portion 130 will reside in the steering plane 28 of the catheter end portion 18. In the preferred embodiment, the tubular end portion 18 is manufactured by an extrusion process, wherein the marker portion 130 is extruded within the sidewall 124 and includes a fluoroscopically opaque material. The arc subtended by the marker portion 130 is preferably approximately 35°–90°, in order to provide a suitable fluoroscopically visible image, which will appear as a dark stripe generally within the steering plane 28 of the catheter 10.

The composition and concentration of the fluoroscopically opaque material included in the composition of the marker portion 130 have the constraints that the material have approximately the same durometer as the tubing sidewall portions 124. In the preferred embodiment, the catheter end portion tubing material is preferably Pellethane (a polyurethane) and the marker portion 130 includes Pellethane with approximately 30%+/−2% of barium sulfate, tantalum oxide or other suitable material. This composition is similar to that of the marker 100 depicted in FIGS. 10–14 and described hereabove.

FIGS. 18 and 19 depict the marker embodiment 120 of FIGS. 16 and 17 when disposed in a left hand curve 140 (FIG. 18) and a right hand curve 142 (FIG. 19) of a bi-directional steering catheter. FIGS. 18 and 19 are comparable to FIGS. 12 and 13 in that they depict how the orientation of the fluoroscopically visible marker 130 provides information to the user regarding the location and orientation of the end portion 18 of the catheter. For further comprehension of the invention, the marker 130 fluoroscopically appears as a stripe close to the inside surface 144 of the left hand curve 140 of FIG. 18, whereas the marker 130 fluoroscopically appears as a stripe close to the outside surface 146 of the right hand curve 142 of FIG. 19.

Figure 21:
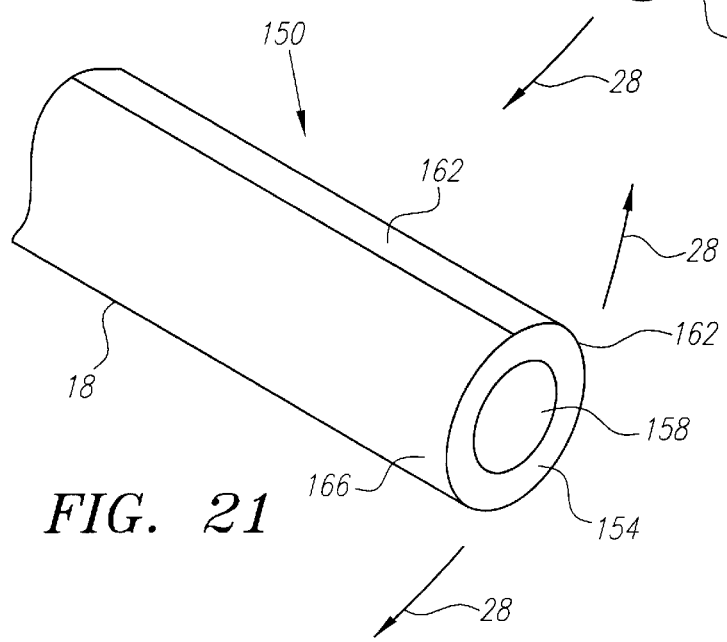
FIG. 21 is a perspective view of the catheter end portion depicted in FIG. 20 and having the tip portion removed therefrom.

FIGS. 20 and 21 depict yet another steering plane marker embodiment 150 of the present invention, wherein FIG. 20 is a perspective view of a catheter end portion 18 having a tip 20 engaged thereto, and FIG. 21 is a perspective view showing the catheter distal end portion 18 with the tip 20 removed. The steering marker embodiment 150 includes a tubular catheter end portion 18 including a cylindrical sidewall 154 and a centrally disposed steering mechanism bore 158. A marker means 162 is disposed on the outer surface 166 of the sidewall 154, and includes a material having enhanced fluoroscopic visibility over the material which comprises the sidewall 154. In the preferred embodiment, the tubular end portion 18 is manufactured utilizing the typical extrusion process and the marker 162 is thereafter applied as a stripe to the outer surface 166 of the tubular end portion 18. The marker stripe 162 is composed of a radiopaque ink or paint that provides a good contrast to the fluoroscopic image of the tubular sidewall 154. In the preferred embodiment, the marker stripe 162 is applied to the tubular end portion 18 in the steering plane 28. Because the radiopaque marker stripe 162 will experience in vivo blood contact, it is important that the marker stripe 162 be tightly adhered to the surface of the catheter end portion 18, that it have approximately the same durometer as the catheter material, and that it be bio-compatible with the patient. In the preferred embodiment, the marker stripe 162 is comprised of a platinum containing adhesive, epoxy or urethane based material.

Figure 22:
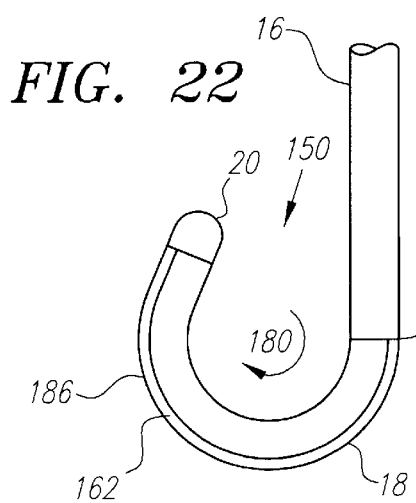
FIG. 22 is a side elevational view of a catheter end portion including the embodiment depicted in FIGS. 20 and 21 in a left hand curve.
Figure 23:
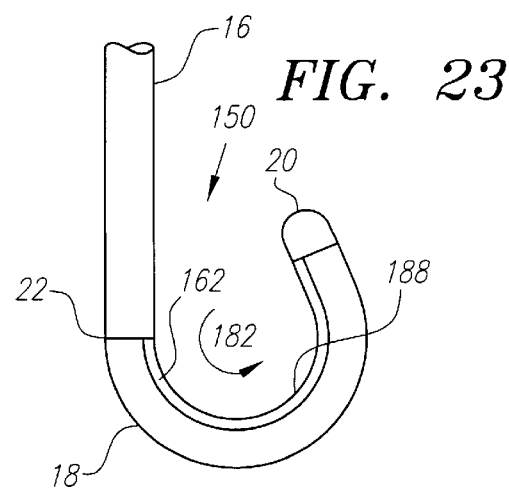
FIG. 23 is a side elevational view of a catheter end portion including the embodiment depicted in FIGS. 20 and 21 in a right hand curve.

FIGS. 22 and 23 depict the marker embodiment 150 of FIGS. 20 and 21 when disposed in a left hand curve 180 (FIG. 22) and a right hand curve 182 (FIG. 23) of a bi-directional steering catheter. FIGS. 22 and 23 are comparable to FIGS. 12 and 13 in that they depict how the orientation of the fluoroscopically visible marker 162 provides information to the user regarding the location and orientation of the end portion 18 of the catheter. For further comprehension of the invention, the marker 162 is shown disposed on the outside surface 186 of the left hand curve 180 of FIG. 22, whereas the marker 162 is shown on the inside surface 188 of the right hand curve 182 of FIG. 23.

FIGS. 24, 25 and 26 depict yet a further steering plane marker embodiment 190 of the present invention, wherein FIG. 24 is a perspective view of the catheter end portion 18 having a catheter tip 20 engaged thereto, FIG. 25 is a top plan view of embodiment 190 depicted in FIG. 24, and FIG. 26 is an end elevational view of the embodiment 190 depicted in FIG. 24. The steering plane marker embodiment 190 includes a tubular catheter end portion 18 having a tip 20 engaged thereto. The marker means includes two generally cylindrical marker plugs 192 and 194 that are disposed within the tip 20 in a similar manner to marker plug 34, as is described hereabove with the aid of FIGS. 2–5. A significant difference between embodiment 190 and embodiment 30 is that embodiment 190 includes two marker plugs (194 and 196), whereas embodiment 30 includes one marker plug (34). With specific reference to embodiment NW, marker plug 192 is disclosed in the steering plane 28 of the tip 18, whereas marker plug 194 is disposed out of the steering plane 28, and generally at a 90° angle to the steering plane 28. Additionally, as is best seen in FIG. 25, marker plug 194 is disposed at a different distance from the distal end 196 of tip 20 than marker plug 192, and in specific regard to embodiment 190, marker plug 192 is disposed closer to distal end 196 than is marker plug 194.

FIGS. 27 and 28 depict the marker embodiment 190 of FIGS. 24, 25 and 26 when disposed in a left hand curve 198 (FIG. 27) and a right hand curve 200 (FIG. 28) of a bi-directional catheter. FIGS. 27 and 28 are comparable to FIGS. 4 and 5 in that they depict how the orientation of the fluoroscopically visible marker 192 provides information to the user regarding the location and orientation of the tip portion 20 of the catheter. For further comprehension of the invention, the marker 192 is shown disposed on the inside surface 202 of the left hand curve 198 of FIG. 27, whereas the marker 192 is shown on the outside surface 204 of the right hand curve 200 of FIG. 28. Furthermore, the out-of-plane plug marker 194 is shown facing the viewer in both FIGS. 27 and 28.

FIG. 29 depicts a side elevational view of the right hand curve catheter configuration depicted in FIG. 28, taken along lines 29—29 thereof. As depicted in FIG. 29, the fluoroscopically visible marker 192 is centrally oriented. It will be that FIG. 29 is an in-plane view, and that other in-plane views will create a substantially identical viewing of the marker 192 of the curved catheter end portion 18. It is therefore to be appreciated that the user will have difficulty determining the orientation of the curved catheter end portion 18 from an in-plane view of marker plug 192. To remove some of the fluoroscopic viewing ambiguity, the out-of-plane marker plug 194 is provided. As depicted in FIG. 29, the out-of-plane orientation of the marker plug 194 provides additional fluoroscopic viewing information to the user regarding the orientation of the curved end portion 18 of the catheter, thus providing an improved performance for the user.

FIGS. 30, 31 and 32 depict still another steering plane marker embodiment 210 of the present invention, wherein FIG. 30 is a perspective view of the catheter end portion 18 having a catheter tip 20 engaged thereto, FIG. 31 is an end elevational view of the steering marker embodiment 210 depicted in FIG. 30, and FIG. 32 is a perspective view showing the catheter end portion 18 with the tip 20 removed. The steering marker embodiment 210 includes a tubular catheter end portion 18 including a cylindrical sidewall 212 having a centrally disposed steering mechanism bore 214. The marker means includes an arcuate marker portion 216 of the sidewall 212 that is disposed in the bi-directional steering plane 28 of the catheter end portion 18. The marker portion 216 includes a material having enhanced fluoroscopic visibility over the material which comprises the remaining portion 218 of the sidewall 212. It is to be appreciated upon a comparison of FIGS. 11 and 32 that the steering plane marker 216 is substantially identical in form and composition to the steering plane marker 100 depicted in FIGS. 10 and 11 and described in detail hereabove.

The marker means also includes an out-of-plane steering marker 220 to provide further fluoroscopically visible catheter orientation information to the user. In the embodiment 210, the out-of-plane steering marker 220 is formed as a cylindrical plug 220 which is disposed in a cylindrical cavity 222 formed in the side of the catheter tip 20. It is to be appreciated that the marker plug 220 depicted in FIGS. 30 and 31 is substantially similar to the marker plug 34 depicted and described hereabove with reference to FIGS. 2 and 3, and to marker plug 194 depicted and described hereabove with reference to FIGS. 24–29. It is therefore to be understood that the plug 220 is oriented approximately 90° out of the steering plane 28, and that the marker plug 220 is constituted and disposed within the catheter tip 20 in a substantially identical manner to the marker plug 194 described hereabove.

FIGS. 33 and 34 depict the marker embodiment 210 of FIGS. 30, 31 and 32 when disposed in a left hand curve 224 (FIG. 33) and a right hand curve 226 (FIG. 34) of a bi-directional steering catheter. FIGS. 33 and 34 are comparable to FIGS. 12 and 13 in that they depict how the orientation of the fluoroscopically visible marker 216 provides information to the user regarding the location and orientation of the end portion 18 of the catheter. For further comprehension of the invention, the marker 216 is shown disposed on the inside surface 228 of the left hand curve 224 of FIG. 33, whereas the marker 216 is shown on the outside surface 230 of the right hand curve 226 of FIG. 34. Furthermore, the out-of-plane plug marker 220 is shown facing the viewer in both FIGS. 33 and 34.

FIG. 35 depicts a side elevational view of the left hand curve catheter configuration depicted in FIG. 33, taken along lines 35—35 thereof. As depicted in FIG. 35, the fluoroscopically visible marker 216 is centrally oriented, and it appears as a single line. Additionally, it will be appreciated that other in-plane views, such as FIG. 35, will create a substantially identical single line fluoroscopic viewing of the marker 216 of the curved catheter end portion 18. It is therefore to be appreciated that the user will have difficulty determining the orientation of the curved catheter end portion 18 from an in-plane view of the marker stripe 216. To remove some of the fluoroscopic viewing ambiguity, the out-of-plane marker plug 220 is provided. As depicted in FIG. 35, the out-of-plane orientation of the marker 220 provides additional fluoroscopic viewing information to the user regarding the orientation of the curved end portion 18 of the catheter, thus providing an improved performance for the user.

While the two marker embodiments 190 and 210 of the present invention have been described utilizing the specific longitudinal marker 100 of FIG. 10 and the plug markers 34 of FIG. 2 in a 90° orientation relative to each other, it will be appreciated by those skilled in the art that other combinations of in-plane and out-of-plane markers can be utilized to provide similar enhanced visual information to the user. A reason for the selection of the plug marker 34 and linear marker 100 in a two marker embodiment 210 is the significantly different visual appearance of them.

Figure 36:
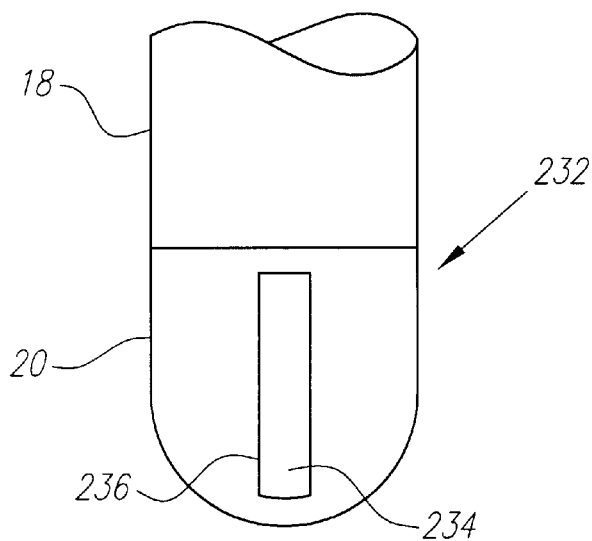
FIG. 36 is a top view of another steering plane marker embodiment of the present invention.
Figure 37:
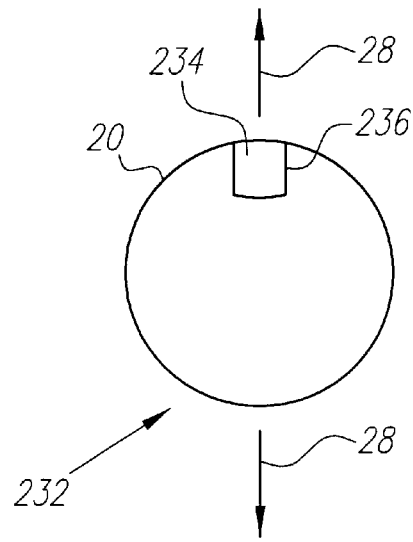
FIG. 37 is an end elevational view of the steering plane marker embodiment depicted in FIG. 36.

A further catheter steering plane marker embodiment 232 his depicted in FIGS. 36 and 37, wherein FIG. 36 is a top view and FIG. 37 is an end elevational view. The generally cylindrical catheter end portion 18 has a rounded catheter tip 20 engaged thereto. A generally rectangular bar shaped steering plane marker means 234 is disposed within a channel 236 formed in the outer surface of the tip 20, such that the marker means 234 resides in the steering plane 28 of the catheter end portion 18. The outer surface of the marker 234 is shaped to smoothly conform with the outer surface of the tip 20. It is therefore to be understood that the steering plane marker embodiment 232 bears significant similarities to the steering plane marker embodiment 30 depicted in FIGS. 2–5 and described hereabove. Preferred marker materials include platinum, barium, bismuth, gold, and other materials that provide a contrasting fluoroscopic image to the material that comprises the remainder of the tip 20.

Figure 38:
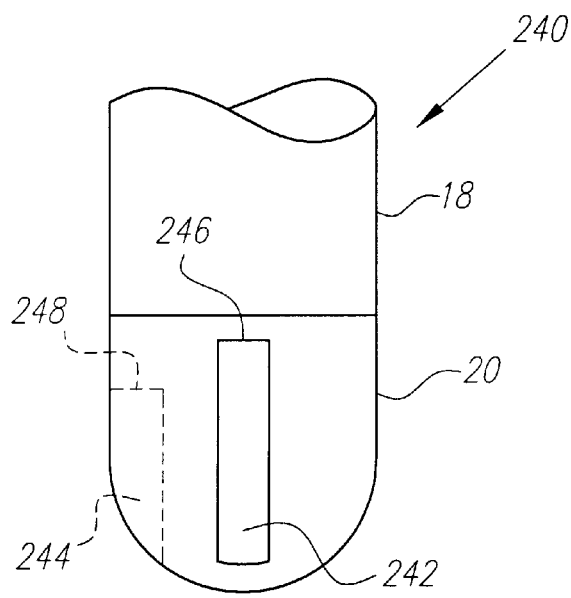
FIG. 38 is a top view of yet another steering plane marker embodiment of the present invention; 22
Figure 39:
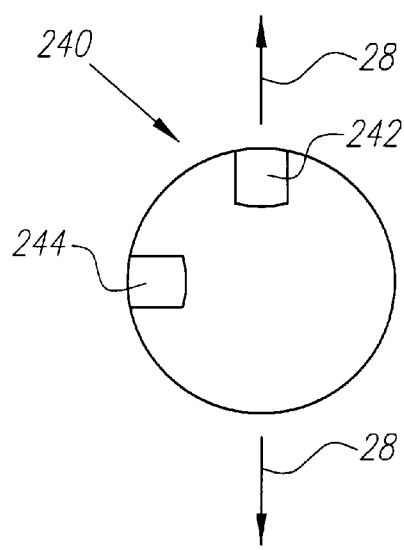
FIG. 39 is an end elevational view of the steering plane marker embodiment depicted in FIG. 38.

FIGS. 38 and 39 depict still a further steering plane marker embodiment 240 of the present invention, wherein FIG. 38 is a top view and FIG. 39 is an end elevational view. The steering plane marker embodiment 240 includes a first generally rectangular marker 242 that is disposed in the steering plane 28 of the catheter distal end portion 18, and an out-of-plane generally rectangular marker 244 that is disposed generally at a 90° angle to the steering plane 28. In the preferred embodiment, one of the markers, such as 242, is formed with a greater length 246 than the length 248 of the other marker 244. The differing lengths serve to distinguish the fluoroscopic images of the two markers 242 and 244. It is to be understood that the two marker embodiment 240 bears great similarity to the two marker embodiment 190 depicted and described hereabove with the aid of FIGS. 24–29, and the utilization of the marker embodiment 240 will be well understood by those of ordinary skill in the art upon comprehension of the utilization of marker embodiment 190.

The markers of the present invention, particularly the marker stripes 100 and 162, can also be used to provide a fluoroscopically visible indication of the location of sensors and other components within the distal end portion 18 of the catheter. FIGS. 40, 41, 42 and 43 provide four examples of such a usage. As depicted in FIG. 40, a marker stripe 260 is located along the surface of the distal end portion 18, and a ring-shaped sensor component 264, having a sensor 266 disposed therewithin is located within the catheter distal end portion 18. The marker stripe 260 is broken where the component 264 is located. It is therefore to be understood that, when the catheter distal end portion 18 is disposed within a patient and viewed fluoroscopically, the marker stripe will appear to be broken at the location of the sensor 264, thus providing a fluoroscopically visible indication of the location of the sensor component 266.

FIG. 41 depicts another embodiment of a catheter distal end portion 18, having a longitudinal marker stripe 260 in which a sensor component 266 is disposed within the line of the marker stripe 260. To provide a fluoroscopically viable indication of the location of the sensor 266, a further component, such as a ring electrode 270, is disposed next to the sensor 266. When the catheter distal end portion 18 is viewed fluoroscopically, the marker stripe 260 will appear to have a break in it at the location of the ring electrode 270, whereby the location of the sensor 266 will be known to be immediately in front of the break in the fluoroscopically visible marker stripe 260; additionally, the ring itself may contain additional fluoromarker materials.

FIG. 42 depicts a further catheter distal end portion 18, having a longitudinal marker stripe 260. A sensor component 266 is located within the stripe 260, and a second stripe portion 274 is disposed to cross the longitudinal stripe 260 at the location of the sensor 266. It is therefore to be appreciated that the fluoroscopic viewing of the catheter distal end portion 18 of FIG. 42 will appear as a cross, designating the location of the sensor 266.

FIG. 43 depicts yet another catheter distal end portion 18, having a plurality of ring electrodes 280 disposed therewithin. A longitudinal marker stripe 260 is broken at the location of each of the ring electrodes 280. When the catheter distal end portion 18 of FIG. 43 is viewed fluoroscopically, the marker stripe will appear as a series of broken segments, thus identifying the location of each of the ring electrodes to the viewer.

As will be apparent to those skilled in the art, the marker stripe embodiments depicted in FIGS. 40–43 provide a marker usage that is not necessarily associated with the steering plane of the catheter distal end portion. That is, the usage of the fluoroscopically visible marker to indicate the location of sensors and components within the catheter end distal end portion provides a useful feature for the user of the device.

Figure 44:
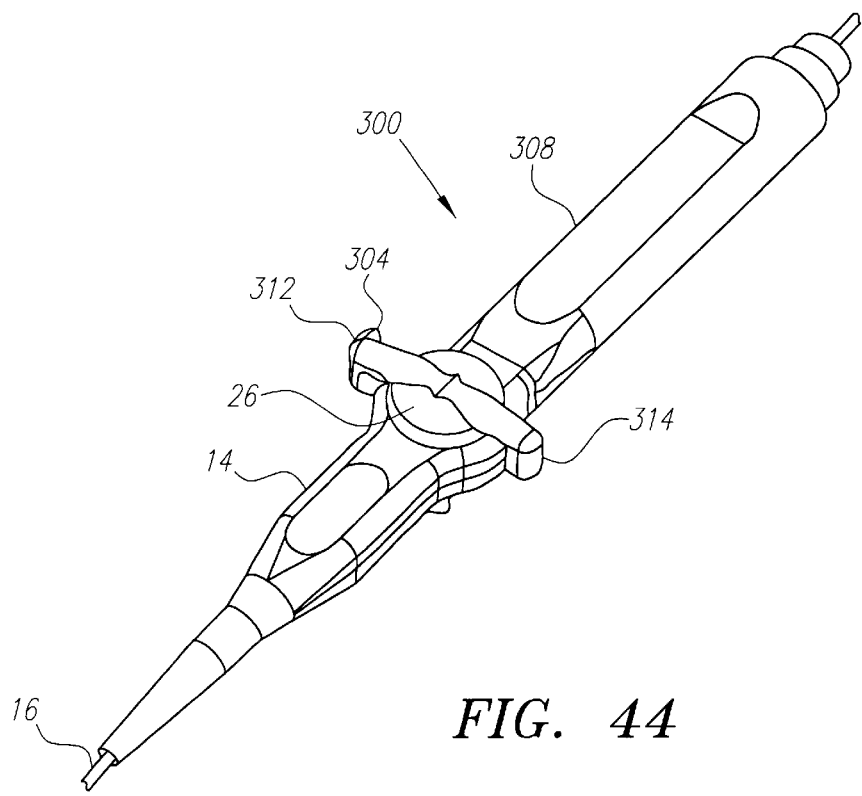
FIG. 44 is a perspective view of a catheter handle depicting a catheter tip orientation marker of the present invention.
Figure 45:
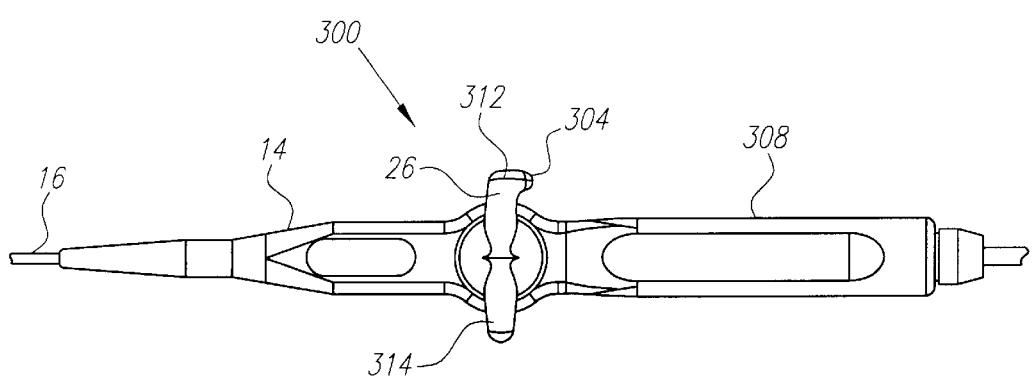
FIG. 45 is a top plan view of a catheter handle depicting the catheter tip orientation marker shown in FIG. 44.

A physician typically watches a fluoroscopic screen while manipulating the handle of a catheter during a medical procedure. An augmented embodiment 300 of the present invention provides a tactile/visual marker 304 on the handle 14, preferably on the control knob 26, to provide further information to the physician regarding the orientation of the control knob 20 in relationship to the orientation of the catheter distal end portion 18. Such a control knob marker 304 is depicted in FIGS. 44 and 45, wherein FIG. 44 is a perspective view of a catheter handle 14, and FIG. 45 is a top plan view thereof.

The improved catheter handle 14 of the present invention includes a hand grip portion 308 and a control knob 26, which has two arms 312 and 314, as are typically found on bi-directional catheter handles, although single arm control knobs are often utilized. As is best seen in FIG. 45, the two control knob arms 312 and 314 are not symmetrical; rather, an identifying tactile marker, specifically a raised bump 304 is formed on the outer surface of arm 312. The marker 304 is located for easy tactile detection by the user of the device. Specifically, the marker 304 is located on arm 312 where the thumb of a right handed user will normally press against it, thus providing the user with a tactile sensation of it. Of course, the location of the marker 304 is but one of several different locations that will suitably provide a user with a tactile sensation of the presence of the marker.

While the present invention has been shown and described with reference to several preferred embodiments, it will be understood by those skilled in the art upon reading the disclosure herein, that certain alterations and modifications in form and detail may be made therein without departing from the true spirit and scope of the invention. It is therefore intended by the inventors that the following claims include all such alterations and modifications that fall within the true spirit and scope of the invention.

What we claim is:

1. A catheter having a tip steering plane marker, comprising:

a handle assembly;

a guide tube being engaged to said handle assembly;

a catheter distal end portion having a steering mechanism disposed therewithin, the steering mechanism operatively connected to said handle assembly;

a marker means being engaged within said end portion, said marker means being comprised of a first material that differs from a second material which comprises said catheter end portion, such that said marker means provides a distinguishable in vivo visual image of the insertion distance and rotational orientation of said catheter distal end portion to a user of said catheter;

wherein said in vivo visual image of the respective insertion distance and rotational orientation of said catheter distal end portion allows said user to make continuous dynamic adjustments to said steering mechanism via manipulation of said handle assembly while simultaneously advancing said catheter through a body cavity.

2. A catheter as described in claim 1 wherein said steering mechanism operates to define a catheter end portion steering plane, and wherein said marker means is disposed, at least in part, within said steering plane.

3. A catheter as described in claim 2 wherein said steering mechanism provides a bi-directional steering capability.

4. A catheter as described in claim 2 wherein said steering mechanism provides a single direction steering capability.

5. A catheter as described in claim 1 wherein said in vivo visual image is accomplished fluoroscopically, and wherein said marker means provides a darker fluoroscopic image than other portions of said catheter end portion.

6. A catheter as described in claim 5 wherein said catheter end portion includes a tip portion and wherein said marker means is disposed within said tip portion.

7. A catheter as described in claim 1 wherein said catheter end portion is generally cylindrical in shape, having a longitudinal central axis thereof, and wherein said marker means is shaped as a linear stripe disposed in a parallel relationship to said longitudinal central axis of said catheter distal end portion.

8. A catheter as described in claim 7 wherein said marker means is disposed within a sidewall of said catheter end portion.

9. A catheter as described in claim 8 wherein said marker means is enclosed within said material that comprises said sidewall of said catheter end portion.

10. A catheter as described in claim 8 wherein said marker means forms an arcuate section of said sidewall.

11. A catheter as described in claim 1, wherein said body cavity is a vein or artery.

12. A catheter as described in claim 1, wherein said handle assembly comprises visual indicia corresponding to the respective insertion distance and rotational orientation of said catheter distal end portion.

13. A catheter as described in claim 1, wherein said handle assembly comprises tactile indicia corresponding to the respective insertion distance and rotational orientation of said catheter distal end portion.

14. A catheter as described in claim 1, wherein said handle assembly comprises a steering control knob, and wherein said in vivo visual image provides information to said user regarding operation said steering control knob.

15. A method of maneuvering a steerable catheter through a body cavity, comprising:

inserting said catheter into said body cavity, said catheter including marker means engaged within a distal end portion of said catheter;

determining the insertion distance and rotational orientation of said catheter distal end portion within said body cavity based on viewing said marker means;

adjusting the path of said catheter distal end portion based on said insertion distance and rotational orientation; and incrementally advancing said catheter through said body cavity.

16. The method of claim 15, wherein said marker means is a fluoroscopically visible material and wherein the insertion distance and rotational orientation of said catheter distal end portion within said body cavity is determined by using a fluoroscope.

17. The method of claim 15, wherein the path of said catheter distal end portion within said body cavity is adjusted by manipulating a control knob located on said catheter.

\* \* \* \* \*